United States Patent
Zhang (10) Patent No.: US 10,393,640 B2
(45) Date of Patent: Aug. 27, 2019

(54) METHOD AND SYSTEM FOR EXHAUST PARTICULATE MATTER SENSING

(71) Applicant: Ford Global Technologies, LLC, Dearborn, MI (US)

(72) Inventor: Xiaogang Zhang, Novi, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 176 days.

(21) Appl. No.: 15/243,754

(22) Filed: Aug. 22, 2016

(65) Prior Publication Data
US 2018/0052091 A1    Feb. 22, 2018

(51) Int. Cl.
G01N 15/06 (2006.01)
F01N 11/00 (2006.01)
G01M 15/10 (2006.01)
G01N 15/00 (2006.01)

(52) U.S. Cl.
CPC ....... *G01N 15/0656* (2013.01); *F01N 11/007* (2013.01); *G01M 15/102* (2013.01); *G01N 15/0606* (2013.01); *F01N 2560/05* (2013.01); *G01N 2015/0046* (2013.01); *Y02T 10/47* (2013.01)

(58) Field of Classification Search
None
See application file for complete search history.

(56) References Cited

U.S. PATENT DOCUMENTS

| 8,341,936 B2 | 1/2013 | Zhang |
| 8,966,956 B2 | 3/2015 | Yoshioka |
| 9,816,426 B2 | 11/2017 | Zhang |
| 10,152,224 B2 | 12/2018 | Fukui |
| 2015/0153249 A1 | 6/2015 | Goulette et al. |
| 2015/0355066 A1 | 12/2015 | Zhang |
| 2015/0355067 A1 | 12/2015 | Zhang et al. |
| 2016/0131013 A1 | 5/2016 | Yi et al. |
| 2016/0223432 A1 | 8/2016 | Kubinski |
| 2017/0146430 A1 | 5/2017 | Zhang |
| 2017/0321587 A1* | 11/2017 | Marlett .................. F01N 9/005 |

\* cited by examiner

*Primary Examiner* — Daniel S Larkin
(74) *Attorney, Agent, or Firm* — Julia Voutyras; McCoy Russell LLP (57) ABSTRACT

Methods and systems are provided for sensing particulate matter by a particulate matter (PM) sensor positioned upstream, or downstream, of a diesel particulate filter in an exhaust system. The PM sensor may include first and second conductive matrixes each having a three dimensional shape. The first matrix functions as a positive electrode, and the second functions as a negative electrode. Each matrix defines extensions and/or passages passing respectively through, and/or near, each other to form multiple soot capturing gaps. A first of the multiple soot capturing gaps is oriented orthogonal to a second of the multiple soot capturing gaps.

11 Claims, 6 Drawing Sheets

METHOD AND SYSTEM FOR EXHAUST PARTICULATE MATTER SENSING

FIELD

The present description relates generally to the design and use of resistive-type particle matter (PM) sensors in an exhaust gas flow.

BACKGROUND/SUMMARY

Diesel combustion may generate emissions, including particulate matter (PM). The particulate matter may include diesel soot and aerosols such as ash particulates, metallic abrasion particles, sulfates, and silicates. When released into the atmosphere, PM can take the form of individual particles or chain aggregates, with most in the invisible sub-micrometer range of 100 nanometers. Various technologies have been developed for identifying and filtering out exhaust PMs before the exhaust is released to the atmosphere.

As an example, soot sensors, also known as PM sensors, may be used in vehicles having internal combustion engines. A PM sensor may be located upstream and/or downstream of a diesel particulate filter (DPF), and may be used to sense PM loading on the filter and diagnose operation of the DPF. Typically, the PM sensor may sense a particulate matter or soot load based on a correlation between a measured change in electrical conductivity (or resistivity) between a pair of thin electrodes placed on a planar substrate surface of the sensor with the amount of PM deposited between the measuring electrodes. Specifically, the measured conductivity provides a measure of soot accumulation.

An example PM sensor is shown by Goulette et. al. in US 2015/0153249 A1. Therein, a conductive material disposed on a substrate is patterned to form interdigitated "comb" electrodes of a PM sensor. When a voltage is applied across the electrodes, soot particles are accumulated at or near the surface of the substrate between the electrodes.

The inventors herein have recognized potential issues with such systems. As an example, in such PM sensors, only a small fraction of the PM in the incoming exhaust experiences the electrostatic forces exerted between the electrodes and gets collected across the electrodes formed on the surface of the sensor, thereby leading to low sensitivity of the sensors. Further, even the fraction of the PM that is accumulated on the surface may not be uniform due to a bias in flow distribution across the surface of the sensor. The PM may tend to accumulate mostly, or strictly, at the inlet side of the sensor, and achieve low, and/or non-uniform soot loading. The non-uniform deposition of the PM on the sensor surface may further exacerbate the issue of low sensitivity of the sensor.

The inventors have recognized the above issues and have identified an approach to at least partly address the issues. In one example, the issues above may be addressed by a particulate matter sensor, including: a first conductive matrix having a three dimensional shape defined by non-negligible dimensions in an x-dimension, a y-dimension, and a z-dimension to be charged to a first voltage to function as a positive electrode; and a second conductive matrix having a three dimensional shape defined by non-negligible dimensions in the x-dimension, the y-dimension, and the z-dimension to be charged to a second voltage to function as a negative electrode. One of the first and second matrices may define extensions and/or passages, and the other of the first and second matrices may define extensions and/or passages. The extensions and/or the passages may pass respectively through, and/or near, each other forming multiple soot capturing gaps defined by a local shortest distance from the first matrix to the second matrix. A first of the multiple soot capturing gaps may be oriented orthogonal to a second of the multiple soot capturing gaps. A change in voltage of the first and/or second matrix may be effected by soot forming in the soot capturing bridges and may be determinable as a soot concentration level in an exhaust stream from an engine. In this way, soot capture may be better distributed and more uniform, and the sensitivity and reliability of the sensor may be improved.

As one example, an exhaust PM sensor assembly may be positioned downstream of an exhaust particulate filter in an exhaust passage. The PM sensor assembly may be a box-type sensor and may include sealed bottom, top, and side surfaces, and may further include open front, and rear surfaces, for directing exhaust inside and out of the assembly.

Overall, these characteristics of the sensor assembly may cause an output of the sensor assembly to be more accurate, thereby increasing the accuracy of estimating particulate loading on a particulate filter.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1:
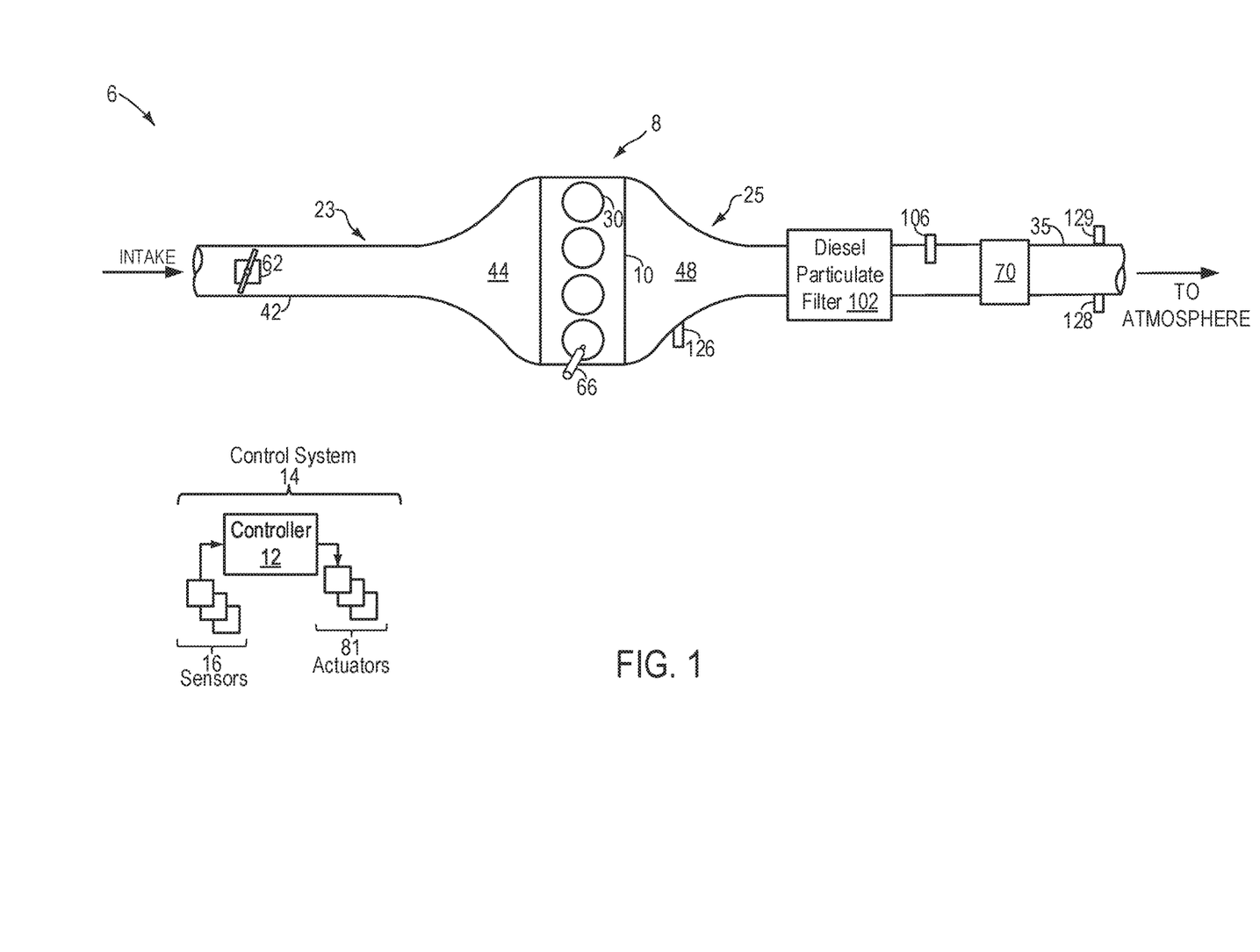
FIG. 1 shows a schematic diagram of an engine and an associated particulate matter (PM) sensor positioned in an exhaust flow.

The following description relates to embodiments of a particulate matter sensor including systems and methods for sensing particulate matter (PM) in an exhaust flow of an engine system, such as the engine system shown in FIG. 1. Embodiments may include a controller 12 that may be configured to perform one or more control routines, to aid, or accomplish various engine operations which may include one or more routines to accumulate exhaust PM across electrodes formed in accordance with the present disclosure. Effective and well distributed accumulation of the PM by the embodiments disclosed herein may cause an output of the PM sensor to be more accurate, thereby increasing the accuracy of estimating particulate loading on a particulate filter. In addition, by enabling more accurate diagnosis of the particulate filter, exhaust emissions compliance may be improved. As such, this may reduce warranty costs associated with replacing functional particulate filters. In addition, exhaust emissions may be improved and exhaust component life may be extended.

FIG. 1 shows a schematic depiction of a vehicle system 6. The vehicle system 6 includes an engine system 8. The engine system 8 may include an engine 10 having a plurality of cylinders 30. Engine 10 includes an engine intake 23 and an engine exhaust 25. Engine intake 23 includes a throttle 62 fluidly coupled to the engine intake manifold 44 via an intake passage 42. The engine exhaust 25 includes an exhaust manifold 48 eventually leading to an exhaust passage 35 that routes exhaust gas to the atmosphere. Throttle 62 may be located in intake passage 42 downstream of a boosting device, such as a turbocharger (not shown), and upstream of an after-cooler (not shown). When included, the after-cooler may be configured to reduce the temperature of intake air compressed by the boosting device.

Engine exhaust 25 may include one or more emission control devices 70, which may be mounted in a close-coupled position in the exhaust. One or more emission control devices may include a three-way catalyst, lean NOx filter, SCR catalyst, etc. Engine exhaust 25 may also include a diesel particulate filter (DPF) 102, which temporarily filters PMs from entering gases, positioned upstream of emission control device 70. In one example, as depicted, DPF 102 is a diesel particulate matter retaining system. DPF 102 may have a monolith structure made of, for example, cordierite or silicon carbide, with a plurality of channels inside for filtering particulate matter from diesel exhaust gas. Tailpipe exhaust gas that has been filtered of PMs, following passage through DPF 102, may be measured in a Particulate Matter (PM) sensor 106 and may be further processed in emission control device 70 and expelled to the atmosphere via exhaust passage 35. In the depicted example, PM sensor 106 may be a resistive sensor that may be configured to estimate the filtering efficiency of the DPF 102 based on a change in conductivity measured across the electrodes of the PM sensor 106.

The vehicle system 6 may further include control system 14. Control system 14 is shown receiving information from a plurality of sensors 16 and sending control signals to a plurality of actuators 81. As one example, sensors 16 may include exhaust flow rate sensor 126 configured to measure a flow rate of exhaust gas through the exhaust passage 35, exhaust gas sensor (located in exhaust manifold 48), temperature sensor 128, pressure sensor 129 (located downstream of emission control device 70), and PM sensor 106. Other sensors such as additional pressure, temperature, air/fuel ratio, exhaust flow rate and composition sensors may be coupled to various locations in the vehicle system 6. As another example, the actuators may include fuel injectors 66, throttle 62, DPF valves that control filter regeneration (not shown), a motor actuator controlling PM sensor opening (e.g., controller opening of a valve or plate in an inlet of the PM sensor), etc. As yet another example, the actuators may include switches coupled to PM measurement circuitry. The control system 14 may include a controller 12. The controller 12 may be configured with computer readable instructions stored on non-transitory memory. The controller 12 may receive signals from the various sensors, may process the signals, and may employ various actuators of to adjust engine operation based on the received signals and instructions stored on a memory of the controller 12. As an example, while operating the PM sensor 106 to accumulate soot particulates, the controller 12 may send one or more control signals to an electric circuit to apply a voltage to electrodes of a sensor element of the PM sensor 106 assembly to trap the charged particulates onto the surface of sensor electrodes of a sensor element. As another example, during PM sensor 106 regeneration, the controller 12 may send a control signal to a regeneration circuit to close a switch in the regeneration circuit for a threshold time to apply a voltage to a heating element (not shown) coupled to electrodes to heat the electrodes of the sensor element. In this way, the electrodes are heated to burn off soot particles deposited on the surface of the electrodes.

Figure 2A:
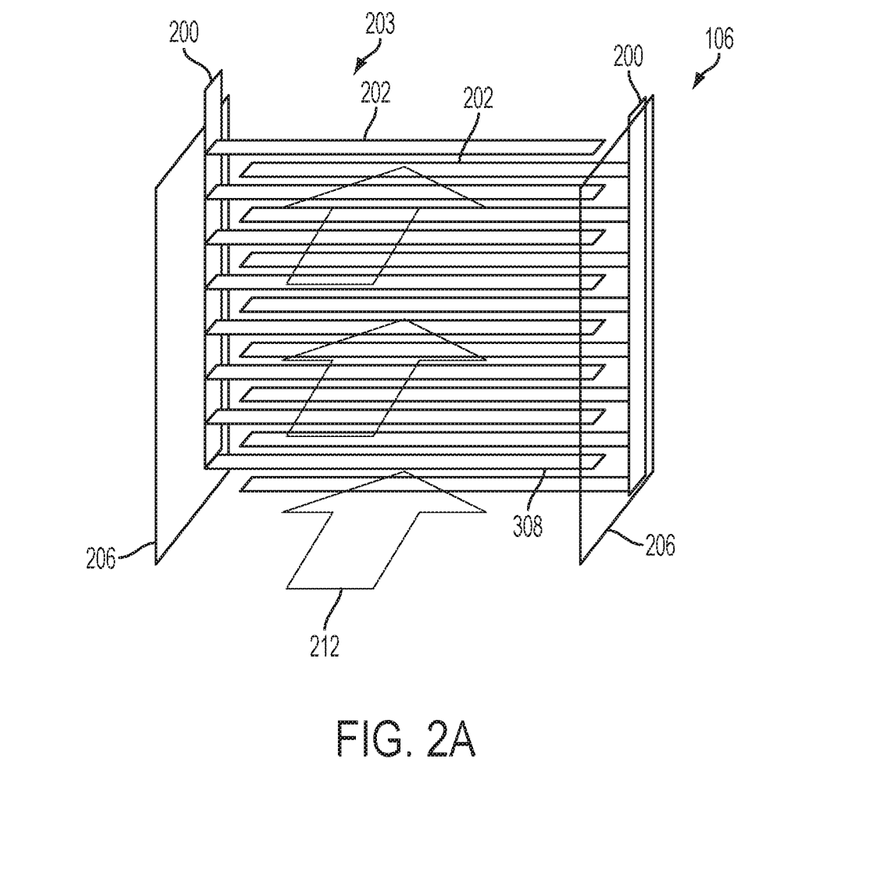
FIG. 2A is a partial schematic perspective view of the PM sensor showing electrically conductive elements in the form of a downstream set of interdigitated comb-like teeth.
Figure 2B:
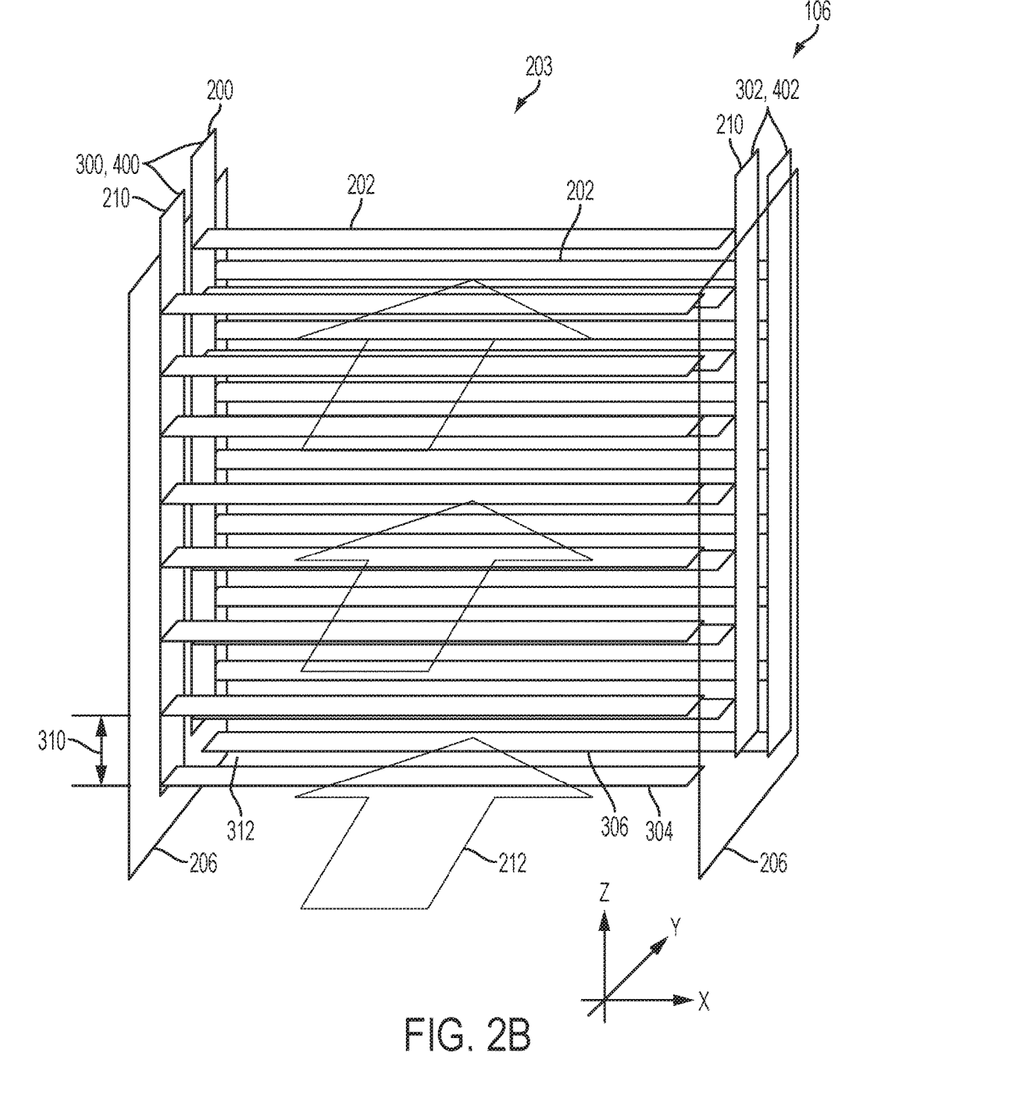
FIG. 2B is a more complete schematic perspective view of the PM sensor shown in FIG. 2A.
Figure 2C:
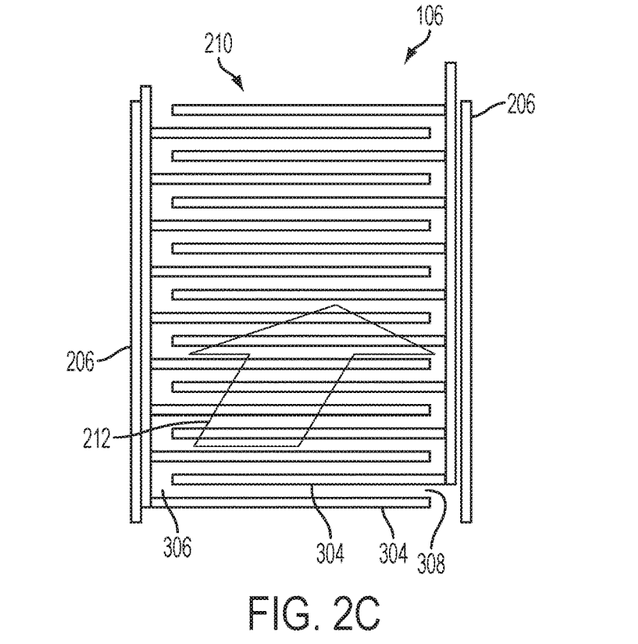
FIG. 2C is a front view of the sensor shown in FIG. 2B.
Figure 2D:
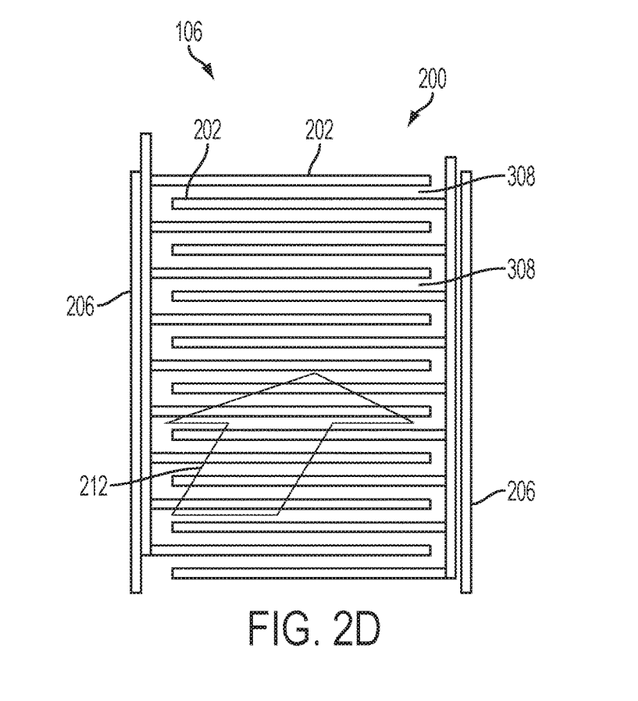
FIG. 2D is a front view of the sensor shown in FIG. 2A.

Turning now to FIGS. 2A-2D, schematic views of portions of an example embodiment of a particulate matter (PM) sensor 106 are shown. Specifically, FIG. 2A is a partial schematic perspective view of the PM sensor 106 showing electrically conductive elements in the form of a downstream set 200 of interdigitated comb-like teeth, or tines 202, in an example boxlike structure with side walls 206 illustrated. The interdigitated comb-like teeth, or tines 202, may be, or may be part of, a matrix 203 of electrically conductive material. FIG. 2D is a front view of the sensor 106 shown in FIG. 2A.

FIG. 2B is a more complete schematic perspective view of the PM sensor 106 shown in FIG. 2A, and FIG. 2C is a front view of the same. FIGS. 2B and 2C also include more electrically conductive elements in the form of an upstream set 210 of interdigitated comb-like teeth, or tines 202, in the example boxlike structure 204. Arrows illustrate an exhaust stream flow direction 212.

Figure 3A:
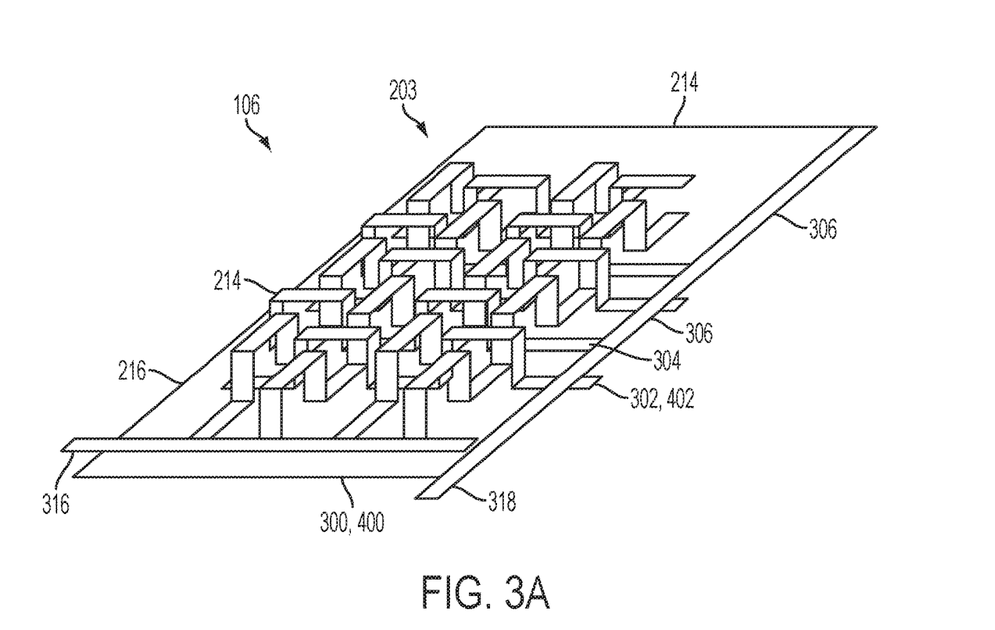
FIG. 3A is a schematic views of another example embodiment of a PM sensor in accordance with the present disclosure.
Figure 3B:
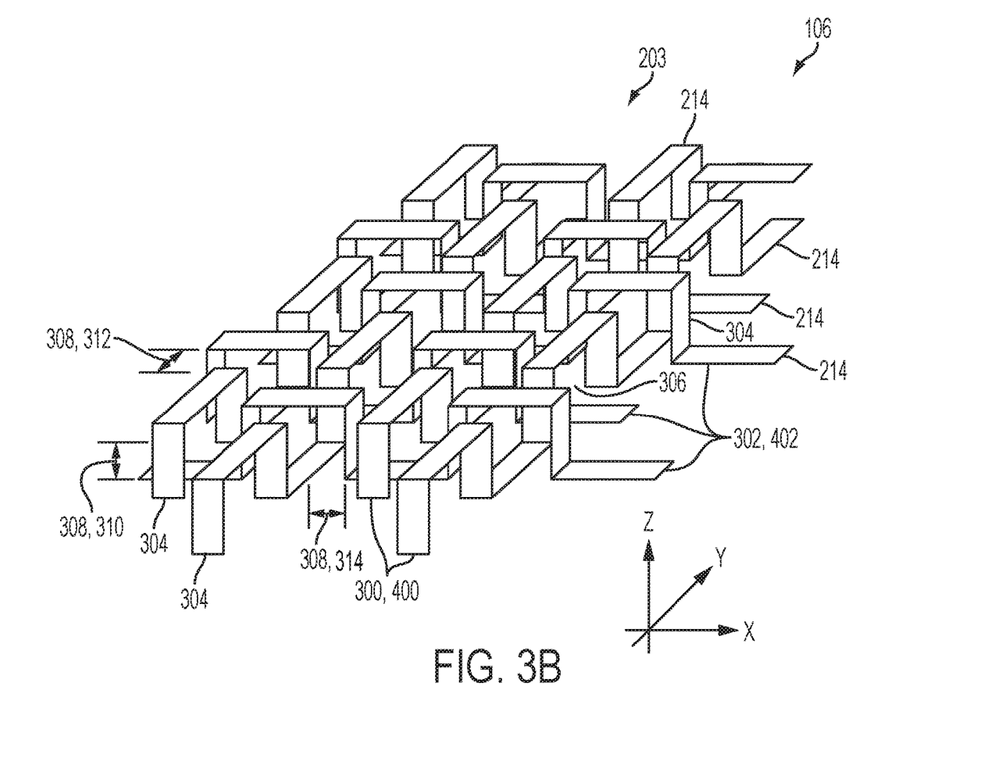
FIG. 3B is a schematic views of an example portion of a PM sensor in accordance with the present disclosure.

FIGS. 3A-3B, are schematic views of another example embodiment of a particulate matter (PM) sensor 106 in accordance with the present disclosure. Another example of a matrix 203 of electrically conductive material in accordance with the present disclosure is also illustrated. Electrically conductive elements make take the form of a plurality of interposed, or interwoven, elongate elements 214. FIG. 3A illustrates interwoven elongate elements 214 positioned on, or coupled with, a substrate 216, or other support mechanisms. FIG. 3B illustrates an example of interwoven elongate elements 214 in accordance with the present disclosure which may be coupled with the same or similar substrate, or may be a portion of a larger matrix of electrodes, repeated, for example, in step-wise fashion any number of times to form a larger matrix 203 of electrically conductive material.

Figure 4:
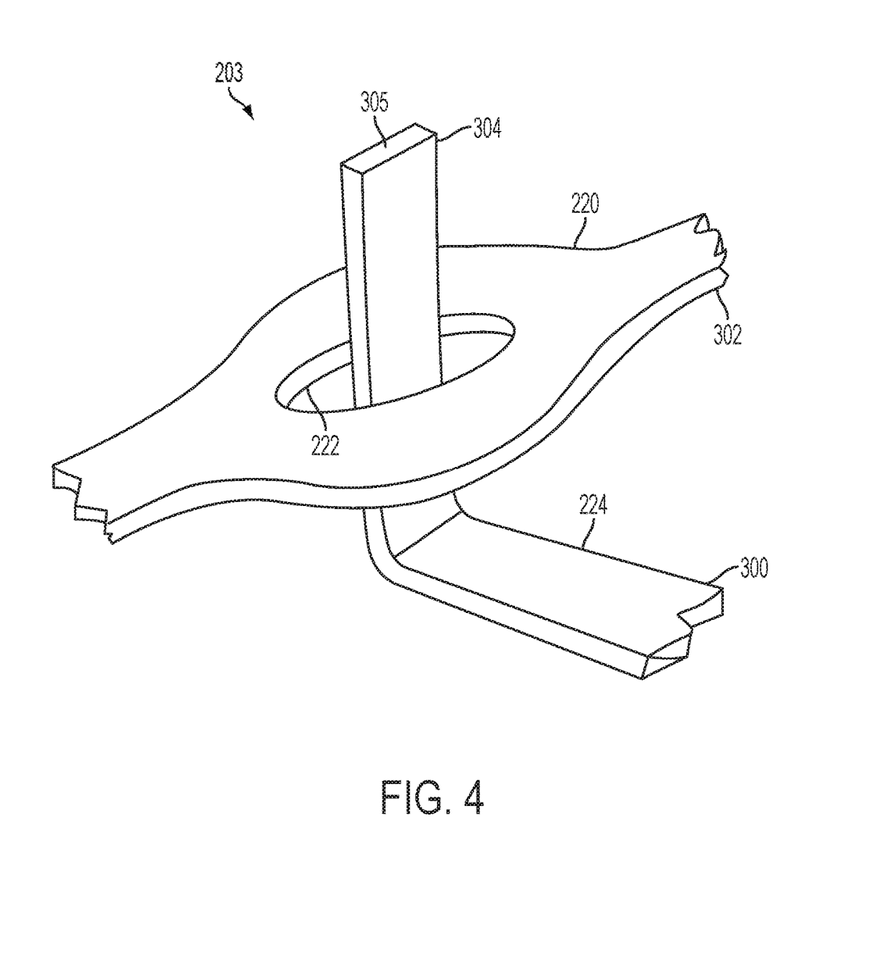
FIG. 4 is a perspective view illustrating a portion of another example matrix of electrically conductive material included in a PM sensor in accordance with the present disclosure.

FIG. 4 is a perspective view illustrating a portion of another example matrix 203 of electrically conductive material. A first electrically conductive element 220 may define one or more holes 222 therethrough. A second electrically conductive element 224 may be disposed to pass into, or through the hole(s) 222. As shown in FIG. 4, the elements are planar, flat, and have a substantially constant thickness. The end 305 passing through hole 222 does so without touching the inner walls of the hole.

Referring again to FIGS. 2A-2D, and FIGS. 3A-3B, in particular FIGS. 2B and 3A-3B, example embodiments may include a particulate matter sensor 106 that may include a first conductive matrix 300. The first conductive matrix 300 may have a three dimensional shape defined by non-negligible dimensions in an x-dimension, a y-dimension, and a z-dimension to be charged to a first voltage to function as a positive electrode. Embodiments may also include a second conductive matrix 302 having a three dimensional shape defined by non-negligible dimensions in the x-dimension, the y-dimension, and the z-dimension to be charged to a second voltage to function as a negative electrode. The first conductive matrix 300 may include a portion of the upstream matrix 210, and a portion of the downstream matrix 200 discussed above. Similarly, the second conductive matrix 302 may include a portion of the upstream matrix 210 and a portion of the downstream matrix 200 discussed above. It will be appreciated that first matrix 300 may be held to a different electrical potential than the second matrix 302. Each of the matrixes 300, 302 may be formed into various geometries.

Non-negligible dimensions may be defined as, for example, dimensions that may be within an order of magnitude of a dimension of reasonably distinguishable features of the matrixes disclosed, such as a change in direction, or a distinguishable width or length. For example, a non-negligible dimension may be a dimension transverse to a body element greater than the thickness of the body element.

Soot or PM in the exhaust gas is typically charged. Due to electrostatic attraction between the charged PM and the interdigitated electrodes, PM get deposited on the electrodes and form soot bridges across the interdigitated electrodes.

One of the first and second matrices 300, 302 may define extensions 304 and/or passages 306. The other of the first and second matrices 300, 302 may also, or instead, define extensions 304 and/or passages 306. The extensions 304 and/or the passages 306 may pass respectively through, and/or near, each other forming multiple soot capturing gaps 308. An extension 304 may be shaped in such a way as to form a passage 306. For example, FIG. 3B illustrates extensions 304 that change direction to define a shape whereby another extension 304 may pass therethrough thereby forming a passage 306.

Individual soot capturing gaps 308 may be defined as, for example, a local shortest distance from the first matrix 300 to the second matrix 302. One or more gaps may also be considered to be formed from tines 202, i.e. extensions 304 near, but spaced from, one another.

As illustrated in FIG. 2B, a first gap 310, represented with a first dimension, of the multiple soot capturing gaps 308 may be oriented orthogonal to a second gap 312, represented with a second dimension, of the multiple soot capturing gaps 308. A change in voltage of the first matrix 300 and/or second matrix 302 may be effected by soot forming in the soot capturing bridges 308 and may be determinable as a soot concentration level in an exhaust stream from an engine 8 (FIG. 1).

In various embodiments the orientation of the first soot capturing gap 310 may be substantially transverse to the flow direction 212 of the exhaust stream, and the orientation of the second soot capturing gap 312 may be substantially parallel with the general flow direction 212 of the exhaust stream. The extensions 304 of the first conductive matrix 300 may includes a first set of electrically conductive comb-like tines 202, and the extensions 304 of the second conductive matrix 302 may include a second set of electrically conductive comb-like tines 202 interdigitated with the first set of electrically conductive comb-like tines 202.

The first group of the interdigitated comb-like tines 202 may be selected, in alternating order, from the first matrix 300 and the second matrix 302 and arranged substantially orthogonal with a general flow direction 212 of the exhaust stream. A second group of the interdigitated comb-like tines 202 may selected, in alternating order, from the second matrix 302 and the first matrix 300 and arranged substantially parallel with the first group of the interdigitated comb-like tines 202.

The first soot capturing gap 310 may be oriented substantially transverse to the general flow direction 212 from the first matrix 300 to the second matrix 302 within the first group of interdigitated comb-like tines, i.e. the upstream set 210 of interdigitated tines 202. The second soot capturing gap 312 may be oriented substantially in line with the general flow direction 212 from the first matrix 300 to the second matrix 302 and from the first group of interdigitated comb-like tines to the second group of interdigitated comb-like tines 202, i.e. from the upstream set 210 of interdigitated tines 202 to the downstream set 200 of interdigitated tines 202.

Referring again to FIG. 4, various embodiments of the particulate matter sensor 106 may include one or more passages from the first conductive matrix 300 that may include one or more holes 222. One or more extensions 304 from the second conductive matrix 203 may extend into the one or more hole(s) 222. The one or more extensions 304 may extend toward the hole in a direction substantially axial with the hole 222, or in an angular direction. The extension 304 may extend through the hole 222, or an end 305 of the extension may be located at a level of the hole 222, i.e. in line with the material of the second electric contact pair. In some cases the end 305 of extension 304 may be spaced a distance from the hole 222 without passing through the hole 222.

Referring now again to FIGS. 3A-3B, in some embodiments, the extensions 304 from a first conductive matrix 300 and extensions 304 from a second conductive matrix 302 may each define corrugated profiles. The respective corrugated profiles may be interposed, and/or interwoven to form the multiple soot capturing gaps 308, or bridges. The multiple soot capturing gaps 308 may be oriented in differing and various directions. For example, a first gap 310 may be oriented in a first direction, for example orthogonal to a flow direction 212 of the exhaust stream. A second gap 312 may be oriented orthogonal to the first gap 310. A third gap 314 may be orthogonal to both the first gap 310 and the second gap 312. Addition gap directions may be utilized.

Various embodiments may provide a particulate matter (PM) sensor 106 for use in an engine exhaust. The PM sensor 106 may include a positive electrode 400 having multiple extensions, and/or multiple passages, and a negative electrode 402 having multiple conductor extensions 304 and/or multiple passages. The extensions 304 and the passages 306 may pass respectively through, and/or near, each other forming multiple soot capturing gaps 308 between the positive electrode 400 and the negative electrode 402. Each soot capturing gap 308 may have an orientation defined by a local shortest distance between the positive electrode 400 and the negative electrode 402, wherein a first portion of the soot capturing gaps 308 may be orientated substantially orthogonally to a second portion of soot capturing gaps 308.

The positive electrode 300 may be electrically coupled with a main positive electrode 316 (FIG. 3A). The main positive electrode 316 may be fixed to a substrate 216. The negative electrode 302 may be electrically coupled with a main negative electrode 318, which may also be coupled with, or fixed to, the substrate 216. The positive electrode 300 and the negative electrode 302 may be located in a boxlike housing, or in a tube-like housing, or a housing of another shape.

In some cases, each gap 310 from first portion of the soot capturing gaps 308 may be orientated substantially transverse to a flow direction 212 of the engine exhaust. In addition, or alternatively, each gap 312 from the second portion of the soot capturing gaps 308 may be orientated substantially in line with the engine exhaust. The positive electrode 400 may include a first set of extensions 304, and the negative electrode may include a second set of extensions 304 interdigitated with the first set of extensions 304.

Embodiments may provide a PM sensor 106 wherein extensions from the positive electrode 400 and extensions from the negative electrode 402 may each define corrugated profiles. The respective corrugated profiles may be interposed, or interwoven, to form the multiple soot capturing gaps 308. A third portion of the soot capturing gaps 314 may be orientated substantially orthogonally to the first portion and to the second portion of soot capturing electrodes.

Embodiments in accordance with the present disclosure may provide various methods. One example method may include orienting a first set of electric contact pairs in a first direction to accumulate a first set of soot bridges along the first direction. The method may include orienting a second set of electric contact pairs in a second direction orthogonal to the first direction to accumulate a second set of soot bridges along the second direction. The method may also include imparting an electric characteristic to each of the first and second sets of electric contact pairs, and sensing a soot level in a diesel exhaust stream based on measuring a change in the electrical characteristics upon accumulating soot from the exhaust stream at the first and second set of soot bridges. A change in the electrical characteristics may be effected by, or in conjunction with the controller 12. The measuring a change in the electrical characteristics may include measuring an aggregate change in conductivity between a negative electrode portion of each of the first and second electric contact pairs and a positive electrode portion of each of the first and second electric contact pairs.

The orienting first and second sets of electric contact pairs may include interdigitating a first set of electrically conductive comb-like tines with a second set of comb-like tines, and defining the first and second sets of electric contact pairs as localized minimal distances between the first and second sets of comb-like tines. The orienting first and second sets of electric contact pairs may include extending an extending element as a first of the electric contact pairs through or adjacent to a hole defined in a second of the electric contact pairs. The extending element may extend toward the hole, for example in a substantially axial direction, but the end may extend, for example, to a plane of the hole, i.e. to a level of the material of the second electric contact pair.

Various embodiments may include a method that includes orienting a third set of electric contact pairs in a third direction to accumulate a third set of soot bridges along the third direction orthogonal to each of the first direction and the second direction. The sensing may include measuring the change of the electrical characteristic to include the third set of soot bridges. The orienting of a third set of electric contact pairs of electric contact pairs may include interweaving a first set of corrugated electrically conductive extensions with a second set of corrugated electrically conductive extensions and defining the first, second, and third sets of electric contact pairs as localized minimal distances between the first and second corrugated electrically conductive extensions. Various methods may include electrically coupling a first portion of each of the electric contact pairs to a main positive electrode, and electrically coupling a second portion of each of the electric contact pairs to a main negative electrode.

The PM sensor 106 may be configured to measure PM mass and/or concentration in the exhaust gas, and as such, may be coupled to an exhaust passage (e.g., such as the exhaust passage 35 shown in FIG. 1), upstream or downstream of a diesel particulate filter (such as DPF 102 shown in FIG. 1).

The PM sensor 106 with electrodes may be positioned inside a protection tube (not shown) and may include conduits (not shown) within the tube that may direct the exhaust gases towards the electrodes. The electrodes may be manufactured from metals such as platinum, gold, osmium, rhodium, iridium, ruthenium, aluminum, titanium, zirconium, and the like, as well as, oxides, cements, alloys and combination comprising at least one of the foregoing metals. The electrodes may be formed on a substrate of the PM sensor 106 that may be manufactured from highly electrically insulating materials. Possible electrically insulating materials may include oxides such as alumina, zirconia, yttria, lanthanum oxide, silica, and combinations comprising at least one of the foregoing, or any like material capable of inhibiting electrical communication and providing physical protection for the pair of interdigitated electrodes.

The PM sensor 106 substrate may include a heating element (not shown) and the PM sensor may be regenerated by heating the sensor substrate via the heating element to burn the accumulated soot particles from the surface of PM sensor 106. By intermittently regenerating the surface of PM sensor 106, it may be returned to a condition more suitable for collecting exhaust soot. In addition, accurate information pertaining to the exhaust soot level may be inferred from the sensor regeneration and relayed to the controller.

Further, the voltage source and the measurement device of the electric circuit may be controlled by a controller, such as controller 12 of FIG. 1, so that particulate matter collected at the PM sensor may be used for diagnosing leaks in the DPF, for example. As such, the measurement device may be any device capable of reading a resistance change across the electrodes, such as a voltmeter. As PM or soot particles get deposited between the electrodes, the resistance between the electrode pair may start to decrease, which may be indicated by a decrease in the voltage measured by the measurement device. The controller 12 may be able to determine the resistance between the electrodes as a function of voltage measured by the measurement device and infer a corresponding PM or soot load on the electrodes of the PM sensor 106. By monitoring the load on the PM sensor 106, the exhaust soot load downstream of the DPF may be determined, and thereby used to diagnose and monitor the health and functioning of the DPF. In some examples, the controller 12 may adjust the voltage source to supply a certain voltage to the electrodes of the PM sensors. When switches are disposed in the electric circuit, the controller 12 may determine the closing and opening of the switches based on a condition of the PM sensor. For example, when the PM sensor is collecting PM, the switches in the circuitry may be adjusted so that voltages are applied to the electrodes of the sensor. However, when the PM sensor is regenerating, the switches connecting the electrodes to the voltage source may be opened. Further, the heating circuit may be turned on by the controller.

In this way, a more accurate measure of the exhaust PM load, and thereby the DPF soot load can be determined. As such, this improves the efficiency of filter regeneration operations, and reduces the need for extensive algorithms. In addition, by enabling more accurate diagnosis of an exhaust DPF, exhaust emissions compliance may be improved. As such, this reduces the high warranty costs of replacing functional particulate filters and exhaust emissions are improved and exhaust component life is extended. In this way, by Instructions for carrying out methods in accordance with the present disclosure may be executed by the controller 12 and may be based on instructions stored on a memory of the controller 12 and may be effected in conjunction with signals received from sensors of the engine system, such as the sensors described above with reference to FIG. 1. The controller 12 may employ engine actuators of the engine system to adjust engine operation, according to the methods described below.

Systems and methods in accordance with the present disclosure may include determining and/or estimating engine operating conditions including exhaust flow conditions. Engine operating conditions determined may include, for example, engine speed, exhaust flow direction, exhaust flow rate, engine temperature, exhaust air-fuel ratio, exhaust temperature, duration (or distance) elapsed since a last regeneration of the DPF, PM load on PM sensor, boost level, ambient conditions such as barometric pressure and ambient temperature, etc. Exhaust flow conditions include estimating or sensing one or more of soot load of PM sensor assembly, exhaust flow rate, exhaust flow direction, exhaust temperature, and the like.

Embodiments may include a heating element coupled to the controller 12. The controller may include, or may utilize, computer readable instructions which may be stored on a non-transitory memory. During exhaust flow, the controller 12 may implement instructions to apply a first voltage to the positive electrode and a second voltage to the negative electrode to accumulate exhaust particulate matter in the exhaust flow across the gaps 308. The controller 12 may receive signals from the PM sensor 106 to estimate a soot load on the particulate matter sensor assembly based on a current generated across the positive and the negative electrode. In some cases, in response to a soot load being higher than a threshold, a voltage may be applied to the heating element of the sensor assembly to regenerate the sensor assembly.

FIGS. 2-4 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

In another representation, an example method comprises generating a first electric field in a first direction to accumulate a first set of soot bridges along the first direction; generating a second, orthogonal electric field in a second direction to accumulate a second set of soot bridges along the second direction, the first direction orthogonal to the second direction; and sensing a soot load of a sensor based on each of the first set of soot bridges and the second set of soot bridges. The example method may include one or more of, or each of, generating a third electric field to accumulate a third set of soot bridges along a third direction, the third direction orthogonal to each of the first direction and the second direction, and adjusting the sensed soot load based on the third set of soot bridges accumulated along the third direction, where each of the first electric field, the second electric field, and the third electric field are generated between positive and negative electrodes forming multiple cross-over pattern on a surface of the assembly.

In another representation, an example particulate matter sensor comprises positive electrodes extending orthogonal to a first substrate; negative electrodes extending orthogonal to a second substrate and interdigitated with the positive electrodes, the second substrate facing towards the first substrate and separated from the first substrate by a gap. In still another example, the particulate matter (PM) sensor, comprises a first substrate extending in a first direction having a first set of electrodes projection out of a surface of the first substrate in a second direction, the second direction being orthogonal to the first direction; and a second substrate positioned at a distance from the first substrate and extending along the first direction, the second substrate having a second set of electrodes projecting out of a surface of the second substrate in a third direction, the third direction opposite to the second direction, wherein optionally the first, second, and third directions are orthogonal to a direction of flow of exhaust, with the first set of electrodes and second set of electrodes interdigitated.

Note that the example control and estimation routines included herein can be used with various engine and/or vehicle system configurations. Selected actions of the control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method, comprising:
    orienting a first set of electric contact pairs in a first direction to accumulate a first soot bridge set along the first direction;
    orienting a second set of electric contact pairs in a second direction orthogonal to the first direction to accumulate a second soot bridge set along the second direction;
    sensing a soot level in diesel exhaust based on electrical characteristics of the first and second sets of electric contact pairs; and
    imparting an electric characteristic to each of the first and second sets of electric contact pairs,
    wherein sensing the soot level in diesel exhaust based on electrical characteristics includes measuring a change in the electrical characteristics and includes measuring an aggregate change in conductivity between a negative electrode portion of each of the first and second sets of electric contact pairs and a positive electrode portion of each of the first and second sets of electric contact pairs.

2. The method of claim 1, wherein orienting the first and second sets of electric contact pairs includes interdigitating a first set of electrically conductive tines with a second set of tines, and defining the first and second sets of electric contact pairs as localized minimal distances between the first and second sets of tines.

3. The method of claim 1, wherein orienting the first and second sets of electric contact pairs includes extending an extending element as a first of the electric contact pairs through or adjacent to a hole defined in a second of the electric contact pairs.

4. The method of claim 1, further comprising orienting a third set of electric contact pairs in a third direction to accumulate a third set of soot bridges along the third direction orthogonal to each of the first direction and the second direction, and wherein the sensing includes measuring a change of electrical characteristics of the first, second, and third sets of soot bridges.

5. The method of claim 4, wherein orienting the first and second sets of electric contact pairs includes interweaving a first set of corrugated electrically conductive extensions with a second set of corrugated electrically conductive extensions and defining the first, second, and third sets of electric contact pairs as localized minimal distances between the first and second corrugated electrically conductive extensions.

6. The method of claim 1, further comprising electrically coupling a first portion of each of the electric contact pairs to a positive electrode, and electrically coupling a second portion of each of the electric contact pairs to a negative electrode.

7. A method, comprising:
    orienting a first set of electric contact pairs in a first direction to accumulate a first soot bridge set along the first direction;
    orienting a second set of electric contact pairs in a second direction orthogonal to the first direction to accumulate a second soot bridge set along the second direction; and
    sensing a soot level in diesel exhaust based on electrical characteristics of the first and second sets of electric contact pairs, wherein orienting the first and second sets of electric contact pairs includes extending an extending element as a first of the electric contact pairs through or adjacent to a hole defined in a second of the electric contact pairs.

8. The method of claim 7, wherein extending the extending element as the first of the electric contact pairs adjacent to the hole includes extending the extending element to a plane of the hole.

9. The method of claim 7, wherein extending the extending element as the first of the electric contact pairs adjacent to the hole includes extending the extending element to a level of a material of the second of the electric contact pairs.

10. A method, comprising:
    orienting a first set of electric contact pairs in a first direction to accumulate a first soot bridge set along the first direction;
    orienting a second set of electric contact pairs in a second direction orthogonal to the first direction to accumulate a second soot bridge set along the second direction;
    sensing a soot level in diesel exhaust based on electrical characteristics of the first and second sets of electric contact pairs; and
    orienting a third set of electric contact pairs in a third direction to accumulate a third set of soot bridges along the third direction orthogonal to each of the first direction and the second direction, and wherein the sensing includes measuring a change of electrical characteristics of the first, second, and third sets of soot bridges.

11. The method of claim 10, wherein orienting the first and second sets of electric contact pairs includes interweaving a first set of corrugated electrically conductive extensions with a second set of corrugated electrically conductive extensions and defining the first, second, and third sets of electric contact pairs as localized minimal distances between the first and second corrugated electrically conductive extensions.

* * * * *